United States Patent [19]
Pusch

[11] Patent Number: 6,077,301
[45] Date of Patent: Jun. 20, 2000

[54] RESILIENT FOOT INSERT FOR AN ARTIFICIAL FOOT

[75] Inventor: Martin Pusch, Duderstadt, Germany

[73] Assignee: Otto Bock Orthopaedische Industrie Besitz- und Verwaltungs-Kommandit-Gesellschaft, Duderstadt, Germany

[21] Appl. No.: 09/064,093

[22] Filed: Apr. 22, 1998

[30] Foreign Application Priority Data

Apr. 24, 1997 [DE] Germany ............... 197 17 298

[51] Int. Cl.⁷ .................................................. A61F 2/66
[52] U.S. Cl. .................................................. 623/53; 623/55
[58] Field of Search ............................. 623/53, 55, 52, 623/47, 40, 27

[56] References Cited

U.S. PATENT DOCUMENTS

| | | | |
|---|---|---|---|
| 4,892,553 | 1/1990 | Prahl | 623/55 |
| 4,959,073 | 9/1990 | Merlette | 623/55 |
| 5,037,444 | 8/1991 | Phillips | 623/55 |
| 5,139,525 | 8/1992 | Kristinsson | 623/55 |
| 5,156,632 | 10/1992 | Wellershaus | 623/55 |
| 5,258,039 | 11/1993 | Goh et al. | 623/55 |
| 5,443,528 | 8/1995 | Allen | 623/52 |
| 5,571,213 | 11/1996 | Allen | 623/52 |
| 5,653,767 | 8/1997 | Allen et al. | 623/52 |
| 5,695,527 | 12/1997 | Allen | 623/55 |
| 5,897,594 | 4/1999 | Martin et al. | 623/53 |

FOREIGN PATENT DOCUMENTS

| | | | |
|---|---|---|---|
| 2 640 499 | 6/1990 | France . | |
| 2 734 151 | 11/1996 | France | 623/55 |
| 40 37 928 | 5/1992 | Germany . | |
| 40 38 063 | 6/1992 | Germany . | |
| 93 15 665 | 1/1994 | Germany . | |
| 9410942 | 5/1994 | WIPO | 623/53 |
| 96/04869 | 2/1996 | WIPO . | |

*Primary Examiner*—Mickey Yu
*Assistant Examiner*—Alvin Stewart
*Attorney, Agent, or Firm*—Foley & Lardner

[57] ABSTRACT

The invention relates to a resilient insert for a jointless artificial foot having a base-spring connected to a C-shaped spring. An articulated link between the opening of the C-shaped spring and the base-spring transfers bending moment forces acting on the C-shaped spring as a result of forefoot loading to the base-spring.

14 Claims, 1 Drawing Sheet

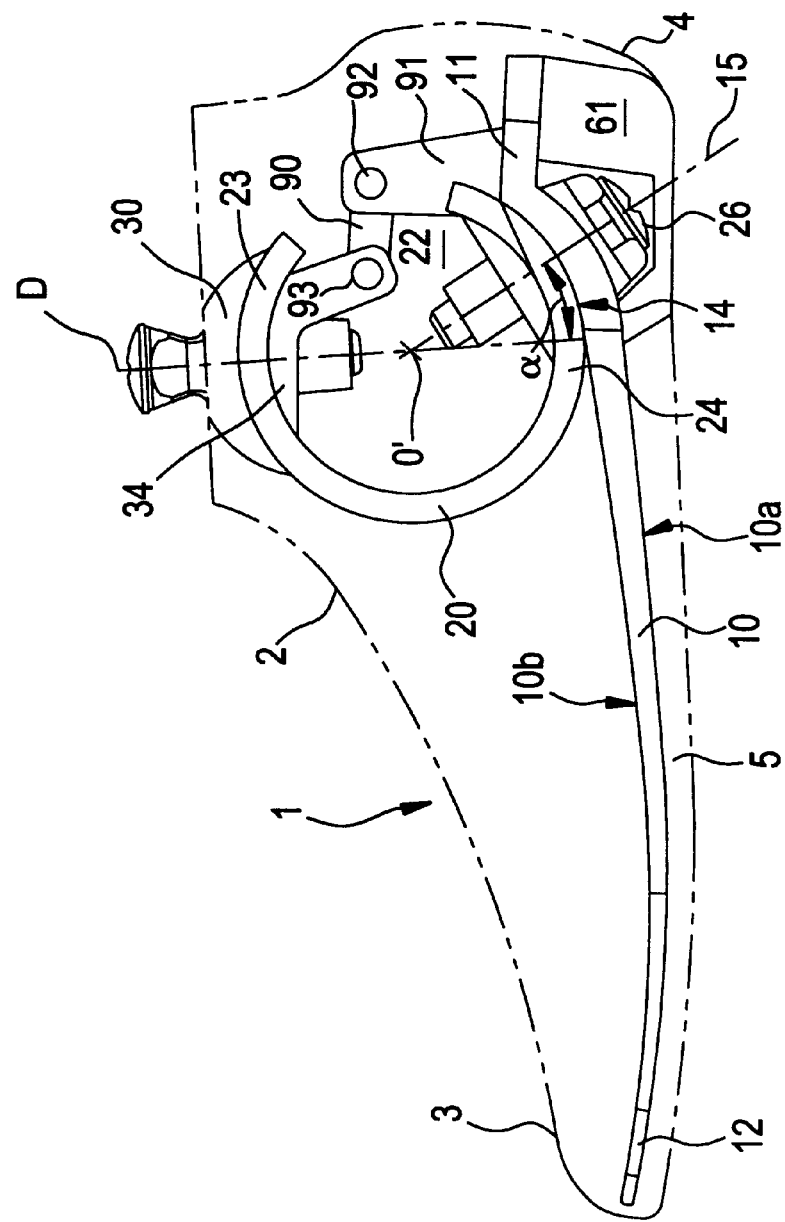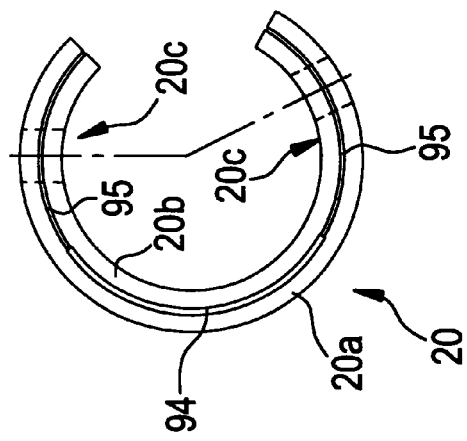

RESILIENT FOOT INSERT FOR AN ARTIFICIAL FOOT

BACKGROUND OF THE INVENTION

1. Field of the Invention

The invention relates to a resilient foot insert arranged within a foot molding of a jointless artificial foot for an artificial leg. According to embodiments of the present invention, a first spring has an approximately C-shaped longitudinal section with an opening facing rearward. A second spring, that is connected to the bottom portion of the C-spring, is a leaf spring that extends forward beyond the C-spring and approximately parallel to the sole region. At a front end, the leaf spring projects as far as the toe region.

2. Description of Related Art

It is known to provide a rigid artificial foot configuration, for example, one made of wood, with or without a joint in order to imitate the function of the ankle. It is also known to provide a resilient foot insert made up of leaf springs and sheathed with foam (see, for example, U.S. Pat. No. 4,959, 073).

German Patent 40 38 063 discloses a jointless prosthetic foot with a one-piece insert that permits plantar and dorsal flection, as well as axial compression, in the longitudinal section of the foot. This patent discloses an approximately S-shaped design having a top portion including a front segment sloping at an obtuse angle, and a generally rigid angle element connecting the front segment to a central, leaf-spring-like portion that is connected at its opposite end to a bottom portion via an approximately semicircular element. In this case, the rigid angle element extends forward, generally into the metatarsophalangeal joint region.

French Patent 26 40 499 discloses a jointless artificial foot in which the central portion of a sideways approximately U-shaped insert is located approximately in the front third of the length of the sole, while a top leg portion of the U-shaped insert forms a connection to the artificial leg. The U-shaped insert assumes a spring function, which is supplemented by a resilient cushion positioned between the legs of the U-shaped insert, for achieving a certain degree of flexibility when the artificial foot is placed on the ground. However, it has been found in practice that this artificial foot does not allow a natural walking motion.

German Utility Model G 93 15 665.0 also discloses a jointless artificial foot including a foamed-plastic foot molding with a metallic reinforcing body having a U-shaped profile whose leg portions can be moved elastically toward one another under loading. The material thickness decreases approaching the free ends of the legs, while the free ends per se are provided with thickened sections. The free end of the bottom leg is screwed to a leaf spring, while the top leg is connected to a leg-connection part. The leaf spring may be made of carbon fiber or titanium. The interspace between the free U-segments may be filled with a flexible polyurethane foam. The intention for this resilient spring element is to allow foot movement in the manner of a pro-oblique supination about the longitudinal axis of the foot, as well as a natural movement sequence.

SUMMARY OF THE INVENTION

One object of the present invention is to provide a jointless artificial foot with improved damping during the act of placing the heel on the ground, improved resilience, improved rolling action and improved lateral stability, thus allowing the user to walk naturally. Another object of the present invention is to enable the user to be capable of both walking normally and doing physical exercises and participating in sports.

In accomplishing the foregoing objects, there has been provided according to the present invention a resilient insert for a jointless artificial foot having a forward toe region, a rearward heel region, a lower sole region extending from the toe region to the heel region, an upper ankle region for connecting to a leg, and an Achilles'-tendon region between the heel region and the ankle region. The resilient insert comprises a first spring having a rearward opening, generally C-shaped cross-section when viewed in a longitudinal, vertical plane; a second spring being connected to the first spring and extending forward from the first spring to a free end in the toe region, the second spring including a saddle on a top side of the second spring receiving a bottom portion of the first spring; an adapter connected to a top portion of the first spring and adapted for releasably connecting the resilient insert to the leg; a bearing block being connected to the second spring rearward of the first spring; and a tie element having a first articulated connection with respect to the top portion of the first spring and a second articulated connection to the bearing block. Preferably, the first spring is a tubular cylinder having a horizontal axis and an axial slit forming the rearward opening, and the second spring is a leaf spring extending approximately parallel to the sole region and having an underside between the first spring and the free end of the second spring that is predominantly convex.

Additional objects, features and advantages of the invention will be set forth in the description which follows, and in part will be obvious from the description, or may be learned by practice of the invention.

BRIEF DESCRIPTION OF THE DRAWINGS

The accompanying drawings, which are incorporated in and constitute a part of the specification, illustrate a presently preferred embodiment of the invention, and, together with the general description given above and the detailed description of the preferred embodiment given below, serve to explain the principles of the invention.

FIG. 1 shows a resilient foot insert in a jointless artificial foot, indicated by chain-dotted lines, in a longitudinal vertical plane of the prothesis.

FIG. 2 shows a modified embodiment of a detail from FIG. 1.

DETAILED DESCRIPTION OF THE PREFERRED EMBODIMENTS

According to preferred embodiments of the present invention:

a) a C-spring may be formed by a horizontally arranged tubular cylindrical segment which has a horizontal cylinder axis and an axial slit forming a rear facing opening;

b) the underside of a base-spring, in the sole region between the C-spring and the base-spring free end, has a predominantly convex shape;

c) the top side of the base spring forms, in the rear end region thereof, a saddle for receiving and securing therein a bottom portion of the C-spring;

d) a top portion of the C-spring is provided with an adaptor for releasably connecting to an artificial leg;

e) the top portion of the C-spring has an articulated connection, via a tie element, to a bearing block which is arranged behind the C-spring and is connected to the rear end of the base spring.

The bearing block may be an integrally formed part of the base-spring and may possibly form the rear terminus of the base-spring. The bearing block may also be supported on a heel wedge, which forms a rear support for the base-spring.

In more preferred embodiments of the present invention, the articulated connection between the tie element and the bearing block is located in the Achilles'-tendon region.

In more preferred embodiments of the present invention, the tie element has an articulated connection to a top pressure plate which butts against the underside of the top portion of the C-spring and is fastened to the adaptor which is supported on the top side of the top portion of the C-spring. In other more preferred embodiments of the present invention, forces may, be transferred directly from the tie element to the adapter via an articulated connection.

According to additional preferred embodiments of the present invention, the tie element and it s articulated connections may be exchanged to change the resilient properties of the foot insert. In particular, the bending moment forces resulting from forefoot loading lead to widening of the mouth of the C-spring. According to embodiments of the present invention, these forces at the mouth of the C-spring are transferred to the base-spring via the tie element. In more preferred embodiments of the present invention, when there is no loading on the insert, the tie element is approximately parallel to the longitudinal axis of the base spring. Thus, the tie element acts in both directions of the C-spring deformation, that is to say, when either the C-spring mouth closes or when it opens. The effect of the tie element is slight in the no-load state since the tie element cannot inhibit the travel when it is perpendicular to the direction of movement of a tie-articulation point. As the inclination of the tie element increases as a result of load deformation on the C-spring, the inhibiting effect which the tie element has on the deformation of the C-spring also increases. For the user, the progression of the tie element produces an easier rolling action onto the forefoot, since the C-spring which is assisted by the tie element according to embodiments of the present invention, may be configured to be more flexible. Thus, the forefoot resistance, which is perceptibly lower for the user, is also reflected in the progression of ankle moments when standing. Changing the inclination, length and/or pre-stressing of the tie makes it possible to adjust the effect between the two progressions of moments depending on the user's requirements.

According to most preferred embodiments of the present invention, the saddle of the base-spring extends upward in a circle-segment form towards the rear end of the base-spring, and the C-spring is releasably fastened to this saddle. In particular, this fastening is located at a distance behind a vertical line through the cylinder axis. Thus, in front of the fastening location, there is a space between the front segment of the bottom portion of the C-spring and the base spring located there beneath, and this space tapers in the form of a wedge towards the fastening location. The resulting spring-deflection region makes an essential contribution to achieving a natural movement sequence.

A jointless artificial foot, according to one preferred embodiment of the present invention illustrated in FIG. 1, has a cosmetic covering 1 which is made of suitable material and defines an ankle region 2, a toe region 3, a heel region 4 and a sole region 5.

A base-spring 10, such as a leaf spring, extends approximately parallel to the sole region 5 and, at its front end 12, projects as far as the toe region 3. The underside 10a of the base spring 10 is convex over the majority of the spring length.

The base-spring 10 is provided with a rear extension 11, starting from which the thickness of the base spring 10 decreases uniformly toward its front end 12. The rear extension 11 merges into a saddle 14, which is defined by the top side 10b of the base spring 10 and has a curved configuration, which may constitute a section of a circle with a center point at 0'.

In addition to the base spring 10, the resilient foot insert also has a C-spring 20 that is received in the saddle 14 and is releasably connected thereto.

The C-spring 20 essentially comprises a tubular cylinder having a generally horizontal cylinder axis 0'.

The C-spring is provided with a comparatively wide, rearward facing, axial slit 22.

The C-spring 20 is secured on the saddle 14 by a fastener, e.g., a screw-bolt 26, having an axis 15 intersecting the center point of the C-spring 20. The center point being coincident with the cylinder axis 0'. FIG. 1 also shows that the fastener 26 is offset to the rear by an angle $\alpha$ with respect to a vertical line D running through 0'. The angle a is preferably between 35° and 45°, and is most preferably 40°. The point of connection between the C-spring 20 and the base spring 10 is thus displaced rearward to a considerable extent with respect to the vertical line D.

A top portion 23 of the C-spring 20 is articulately connected, via a tie element 90, to a bearing block 91 which is arranged behind the C-spring 20. The bearing block 91 is connected to the rear end 11 of the base spring 10 and is supported on a heel wedge 61, which forms the rear support for the base spring 10. A rear articulate connection 92 is located in the Achilles'-tendon region, while a front articulate connection 93 is provided on a top pressure plate 34 which butts against the underside of the top portion 23 of the C-spring 20. The top pressure plate 34 is fastened to an adaptor 30 which is supported on a top side of the top portion 23 of the C-spring 20. FIG. 1 shows that, in the load-free state, the tie element 90 is located approximately parallel to the longitudinal axis of the base-spring 10.

The tie element 90 may comprise a textile strap which, at its two articulated connections 92,93, includes bights guided over in each case one journal. The configuration of these bights on the journals can influence the overall spring characteristics, since different journal radii, upon expansion of the C-spring, result in the tie element shortening or lengthening differently. The journals are thus preferably arranged so as to be exchangeable.

In preferred embodiments of the present invention, the forces which are transmitted to the C-spring by forefoot-loading, can be minimized by moving the bearing block 91 as far as possible to the rear, taking into account of the overall design of the artificial foot.

In preferred embodiments of the present invention, the C-spring 20 may be made from a carbon composite. In more preferred embodiments of the present invention, the fatigue strength of the C-spring, which is necessary for the functionally required deformation, can be increased to absorb with sufficient reliability the stresses which occur by using the C-spring which is illustrated in FIG. 2. This C-spring is made up of two parallel C-spring lamellae 20a and 20b which are positioned concentrically one inside the other. In their end regions 20c, the lamellae 20a and 20b are connected to one another via interposed spacers 95, so as to be rigid with respect to moments. Between these two end regions 20c, the two C-spring lamellae 20a and 20b are spaced apart from one another by a clear radial distance 94. This avoids the situation where, when the C-spring is compressed, the inner lamella 20b comes to butt prematurely against the outer lamella 20a, since the spring characteristics are changed abruptly when such abutment occurs.

By virtue of the parallel C-spring lamellas 20a and 20b, a considerable improvement to the structural strength of the C-spring 20 is achieved without adversely affecting the spring characteristics.

Additional advantages and modifications will readily occur to those skilled in the art. Therefore, the invention in its broader aspects is not limited to the specific details and representative devices shown and described herein. Accordingly, various modifications may be made without departing from the spirit and scope of the general inventive concept as defined by the appended claims and their equivalents.

German Patent Application 197 17 298.9, filed Apr. 24 1997, is hereby incorporated by reference.

What is claimed is:

1. A resilient insert for a jointless artificial foot having a forward toe region, a rearward heel region, a lower sole region extending from the toe region to the heel region, an upper ankle region for connecting to a leg, and an Achilles'-tendon region between the heel region and the ankle region, the resilient insert comprising:

a first spring having a rearward opening, generally C-shaped cross-section when viewed in a longitudinal, vertical plane;

a second spring being connected to said first spring and extending forward from said first spring to a free end in the toe region, said second spring including a saddle on a top side of said second spring receiving a bottom portion of the first spring;

an adapter connected to a top portion of said first spring and adapted for releasably connecting the resilient insert to the leg;

a bearing block being connected to said second spring rearward of said first spring; and a tie element having a first articulated connection with respect to said top portion of said first spring and a second articulated connection to said bearing block, said tie element extending approximately parallel to a longitudinal direction of said second spring when there is no load on the resilient insert.

2. The resilient insert as claimed in claim 1, wherein said first spring is a tubular cylinder having a horizontal axis and an axial slit forming said rearward opening.

3. The resilient insert as claimed in claim 2, further comprising:

a fastener securing said first spring to said saddle of said second spring;

wherein said fastener is located rearward of said horizontal axis.

4. The resilient insert as claimed in claim 1, wherein said second spring is a leaf spring extending approximately parallel to the sole region.

5. The resilient insert as claimed in claim 1, wherein an underside of said second spring between said first spring and said free end of said second spring is predominantly convex.

6. The resilient insert as claimed in claim 1, wherein said second articulated connection is in the Achilles'-tendon region.

7. The resilient insert as claimed in claim 1, further comprising:

a top pressure plate fixed with respect to said adapter, said tie element being connected to said top pressure plate by said first articulated connection;

wherein said adapter is located on a top side of said top portion of said first spring and said top pressure plate is located on a bottom side of said top portion of said first spring.

8. The resilient insert as claimed in claim 1, wherein said tie element is connected to said adaptor by said first articulated connection.

9. The resilient insert as claimed in claim 1, wherein said tie element includes a textile strap.

10. The resilient insert as claimed in claim 9, wherein said first and second articulated connections each include an exchangeable cylindrical segment and said textile strap includes bights encircling respective ones of said exchangeable cylindrical segments.

11. The resilient insert as claimed in claim 1, wherein said first spring includes at least two parallel, concentric, generally C-shaped lamellae, each of said at least two lamellae having a first end portion, a second end portion, and a central portion between said first end portion and said second end portion, wherein:

said first end portion of a first lamella of said at least two lamellae is rigidly connected to said first end portion of a second lamella of said at least two lamellae, said second end portion of said first lamella is rigidly connected to said second end portion of said second lamella, and said central portion of said first lamella is spaced apart from said central portion of said second lamella by a clear radial distance.

12. The resilient insert as claimed in claim 11, further comprising:

spacers between said at least two lamella at said first and second end portions.

13. The resilient insert as claimed in claim 1, further comprising:

a wedge in the heel region supporting an underside of said second spring.

14. The resilient insert as claimed in claim 13, wherein said wedge also supports said bearing block.

* * * * *